United States Patent
Hakonarson et al.

(10) Patent No.: US 9,926,600 B2
(45) Date of Patent: Mar. 27, 2018

(54) GENETIC ALTERATIONS ASSOCIATED WITH TYPE I DIABETES AND METHODS FOR USE THEREOF FOR DIAGNOSIS AND TREATMENT

(71) Applicant: The Children's Hospital of Philadelphia, Philadelphia, PA (US)

(72) Inventors: Hakon Hakonarson, Malvern, PA (US); Joseph Glessner, Mullica Hill, NJ (US); Struan F. A. Grant, Philadelphia, PA (US); Constantin Polychronakos, Cote Saint Luc (CA)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 208 days.

(21) Appl. No.: 14/251,956

(22) Filed: Apr. 14, 2014

(65) Prior Publication Data

US 2015/0023984 A1    Jan. 22, 2015

Related U.S. Application Data

(63) Continuation of application No. 13/123,088, filed as application No. PCT/US2009/059998 on Oct. 8, 2009, now abandoned.

(60) Provisional application No. 61/103,709, filed on Oct. 8, 2008.

(51) Int. Cl.
*C12Q 1/68* (2006.01)
*C07H 21/04* (2006.01)

(52) U.S. Cl.
CPC ..... *C12Q 1/6883* (2013.01); *C12Q 2600/136* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2007/0224638 A1 | 9/2007 | Melanitou-McClymont |
| 2008/0226595 A1 | 9/2008 | Edinger |
| 2008/0227846 A1 | 9/2008 | Singh |

OTHER PUBLICATIONS

Illumina (Analyzing Copy number Variation with the Infinium Whole-Genome Genotyping Assay, 2006).*
Qu et al. (Genome Wide Association of Copy Number Variations (CNVs) in Type 1 Diabetes (T1D) Identifies novel genes in previously associated T1D Pathways, 2008 meeting Abstracts, Nov. 2008).*
Affymetrix.com Genome-Wide Human SNP Array 6.0 (2008).*
Estivill et al (PLos Genetics, vol. 3, No. 10, e190, 1787-1799, Oct. 2007).*
Cucca et al., A correlation between the relative predisposition of MHC class II alleles to type 1 diabetes and the structure of their proteins, Human molecular genetics, 2001, 2025-37, 10(19).
Julier et al., Insulin-IGF2 region on chromosome 11p encodes a gene implicated in HLA-DR4-dependent diabetes susceptibility, Nature, 1991, 155-9, 354(6349).
Barratt et al., Remapping the insulin gene/IDDM2 locus in type 1 diabetes, Diabetes, 2004, 1884-9, 53(7).
Gunderson et al., A genome-wide scalable CNV genotyping assay using microarray technology, Nature genetics, 2005, 549-54, 37(5).
McKinney et al., Evidence for an influence of chemokine ligand 3-like (CCL3L1) gene copy number on susceptibility to rheumatoid arthritis, Ann Rhem Dis., 2008, 409-413, 67.
Bottini et al., A functional variant of lymphoid tyrosine phosphatase is associated with type I diabetes, Nature genetics, 2004, 337-8, 36(4).
Smyth et al., Replication of an association between the lymphoid tyrosine phosphatase locus (LYP/PTPN22) with type 1 diabetes, and evidence for its role as a general autoimmunity locus, Diabetes, 2004, 3020-3, 53(11).
Nistico et al., The CTLA-4 gene region of chromosome 2q33 is linked to, and associated with, type 1 diabetes, Belgian Diabetes Registry, Human molecular genetics, 1996, 1075-80, 5(7).
Ueda et al., Association of the T-cell regulatory gene CTLA4 with susceptibility to autoimmune disease, Nature, 2003, 506-11, 423(6939).
Vella et al., Localization of a type I diabetes locus in the IL2RA/CD25 region by use of tag single-nucleotide polymorphisms, American journal of human genetics, 2005, 773-9, 76(5).
Leiter et al., Mouse models and the genetics of diabetes: is there evidence for genetic overlap between type 1 and type 2 diabetes? Diabetes, 2005, S151-8, 54 Suppl 2.

* cited by examiner

*Primary Examiner* — Jeanine A Goldberg
(74) *Attorney, Agent, or Firm* — Kathleen D. Rigaut; Dann, Dorfman, Herrell & Skillman

(57) ABSTRACT

Compositions and methods for the detection and treatment of T1D are provided.

1 Claim, No Drawings

GENETIC ALTERATIONS ASSOCIATED WITH TYPE I DIABETES AND METHODS FOR USE THEREOF FOR DIAGNOSIS AND TREATMENT

This application is a continuation of U.S. application Ser. No. 13/123,088 filed Jun. 13,2011, which is a § 371 national phase entry of PCT/US2009/059998 filed Oct. 8, 2009, which claims priority to U.S. Provisional Application 61/103,709 filed Oct. 8, 2008, each of the aforementioned applications being incorporated herein by reference.

FIELD OF THE INVENTION

This invention relates to the fields of glucose metabolism, genetics and pathology associated with diabetes, particularly type I diabetes. More specifically, the invention provides a panel of genes containing copy number variations which had heretofore not been associated with this disease. Methods and kits for using the sequences so identified for diagnostic and therapeutic treatment purposes are also provided, as are therapeutic compositions for management of diabetes.

BACKGROUND OF THE INVENTION

Several publications and patent documents are cited throughout the specification in order to describe the state of the art to which this invention pertains. Each of these citations is incorporated herein by reference as though set forth in full.

Type I diabetes (T1D) results from the autoimmune destruction of pancreatic beta cells, a process believed to be strongly influenced by multiple genes and environmental factors. The incidence of T1D has been increasing in Western countries and has more than doubled in the United States over the past 30 years. The disease shows a strong familial component, with first-degree relatives of cases being at 15 times greater risk of T1D than a randomly selected member of the general population and monozygotic twins being concordant for T1D at a frequency of approximately 50%. However, while the genetic evidence is strong, the latter data suggests that an interplay with environmental factors also plays a key role in influencing T1D outcome.

The familial clustering of T1D is influenced by multiple genes. Variation in four loci has already been established to account for a significant proportion of the familial aggregation of T1D. These include the major histocompatibility complex (MHC) region on 6p21 (including the HLA-DRB1, -DQA1 and -DRQ1 genes[1]); the insulin/insulin-like growth factor 2 gene complex (INS-IGF2) on 11p15[2-4], the protein tyrosine phosphatase-22 (PTPN22) gene on 1p13[5, 6] and the gene encoding cytotoxic T-lymphocyte-associated protein 4 (CTLA4) on 2q31[7, 8]. The interleukin-2 receptor alpha (CD25) locus on 10p15[9] has also been implicated in the pathogenesis of T1D but remains to be replicated by independent studies. In addition, spontaneous mouse model studies of T1D have implicated numerous other regions that have been confirmed in replication studies[10]. Several other loci have also been implicated in human association studies with T1D but the effects of these implicated genes remain controversial and are subject to confirmation in independent studies utilizing sufficient sample sizes. Together, these studies suggest that many more T1D susceptibility genes remain to be discovered. It is also clear that there are differences in genetic susceptibility to T1D between populations. An explanation for this variation may be related to differing frequencies of T1D causative and protective variants between different populations and ethnic groups, a hypothesis that needs to be addressed in multi-center, multi-national studies that are truly trans-continental.

SUMMARY OF THE INVENTION

In accordance with the present invention, T1D-associated copy number variations (CNVs) have been identified which are indicative of an increased risk of developing T1D. Thus, in one aspect, nucleic acids comprising at least one genetic alteration identified in Table 1 is provided. Such nucleic acids and the proteins encoded thereby have utility in the diagnosis and management of type 1 diabetes (T1D).

In another aspect of the invention, methods for assessing susceptibility for developing T1D are provided. An exemplary method entails providing a target nucleic acid from a patient sample, said target nucleic acid having a predetermined sequence in the normal population, and assessing said target nucleic acid for the presence of a genetic alteration including one or more copy number variations which is/are indicative of an increased risk of developing T1D. Such genetic alterations include, without limitation, inversion, deletion, duplication, and insertion of at least one nucleotide in said sequence.

Preferably, the genetic alteration is a copy number variation listed in Table 1, the presence of which being associated with an increased risk of developing T1D.

The methods of the invention also include the detection of any of the T1D associated genetic alterations comprising the CNVs set forth in Table 1 for the diagnosis of T1D. Kits and microarrays for practicing the foregoing methods are also provided.

In yet another embodiment, a method of managing T1D is provided which entails administering a therapeutic agent to a patient in need thereof. The therapeutic agent can be a small molecule, an antibody, a protein, an oligonucleotide, or a siRNA molecule.

In another aspect of the invention, a method for identifying agents that bind and/or modulate the functional activity of the protein products encoded by the genes listed in Table 1 is provided, as well as pharmaceutical compositions comprising said agent in a biologically acceptable carrier.

DETAILED DESCRIPTION OF THE INVENTION

In previous studies, a number of genetic determinants of T1D have been established through candidate gene studies, primarily with the major histocompatibility complex (MHC) but also with other loci. As described herein, several new genetic alterations have been discovered which predispose the patient to an increased risk for TID. These results provide evidence for a diverse set of genetic factors that contribute substantially to the pathogenesis of T1D, and thus provide promising new T1D therapeutic and diagnostic targets.

The following definitions are provided to facilitate an understanding of the present invention:

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

A "copy number variation (CNV)" refers to the number of copies of a particular gene in the genotype of an individual. CNVs represent a major genetic component of human phenotypic diversity. Susceptibility to genetic disorders is known to be associated not only with single nucleotide polymorphisms (SNP), but also with structural and other genetic variations, including CNVs. A CNV represents a copy number change involving a DNA fragment that is ~1 kilobases (kb) or larger (Feuk et al. 2006 Hum. Mol. Genet., 15: R57-R66). CNVs described herein do not include those variants that arise from the insertion/deletion of transposable elements (e.g., ~6-kb KpnI repeats) to minimize the complexity of future CNV analyses. The term CNV therefore encompasses previously introduced terms such as large-scale copy number variants (LCVs; Iafrate et al. 2004 *Nature Genetics* 36: 949-51), copy number polymorphisms (CNPs; Sebat et al. 2004 *Science* 305: 525-528.), and intermediate-sized variants (ISVs; Tuzun et al. 2005 Nat Genet. 37:727-32), but not retroposon insertions.

A "single nucleotide polymorphism (SNP)" refers to a change in which a single base in the DNA differs from the usual base at that position. These single base changes are called SNPs or "snips." Millions of SNP's have been cataloged in the human genome. Some SNPs, such as that which causes sickle cell, are responsible for disease. Other SNPs are normal variations in the genome. Finally, some SNPs, are indicative of a predisposition to certain diseases (e.g., T1D).

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence.

The phrase "Type 1 diabetes (T1D)" refers to a chronic (lifelong) disease that occurs when the pancreas produces too little insulin to regulate blood sugar levels appropriately. T1D, often called juvenile or insulin-dependent diabetes results from altered metabolism of carbohydrates (including sugars such as glucose), proteins, and fats. In type 1 diabetes, the beta cells of the pancreas produce little or no insulin, the hormone that allows glucose to enter body cells. Once glucose enters a cell, it is used as fuel. Without adequate insulin, glucose builds up in the bloodstream instead of going into the cells. The body is unable to use this glucose for energy despite high levels in the bloodstream, leading to increased hunger. In addition, the high levels of glucose in the blood cause the patient to urinate more, which in turn causes excessive thirst. Within 5 to 10 years after diagnosis, the insulin-producing beta cells of the pancreas are completely destroyed, and no more insulin is produced.

"T1D-associated CNV or specific marker" is a CNV or marker which is associated with an increased risk of developing TID not found normal patients who do not have this disease. Such markers may include but are not limited to nucleic acids, proteins encoded thereby, or other small molecules. Type 1 diabetes can occur at any age, but it usually starts in people younger than 30. Symptoms are usually severe and occur rapidly. The exact cause of type 1 diabetes is not known. Type 1 diabetes accounts for 3% of all new cases of diabetes each year. There is 1 new case per every 7,000 children per year. New cases are less common among adults older than 20.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose. "Sample" or "patient sample" or "biological sample" generally refers to a sample which may be tested for a particular molecule, preferably an T1D specific marker molecule, such as a marker shown in the table provided below. Samples may include but are not limited to cells, body fluids, including blood, serum, plasma, urine, saliva, tears, pleural fluid and the like.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the functional and novel characteristics of the sequence.

"Target nucleic acid" as used herein refers to a previously defined region of a nucleic acid present in a complex nucleic acid mixture wherein the defined wild-type region contains at least one known nucleotide variation which appears to be associated with T1D. The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{-6}$-fold purification of the native message. Thus, purification of at least one order of magnitude, preferably two or three orders, and more preferably four or five orders of magnitude is expressly contemplated. Thus, the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under predetermined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any T1D specific marker gene or nucleic acid, but does not hybridize to other human nucleotides. Also polynucleotide which "specifically hybridizes" may hybridize only to a T1D specific marker, such a T1D-specific marker shown in Table 1. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., *Molecular Cloning*, Cold Spring Harbor Laboratory (1989):

$$T_m = 81.5° C. + 16.6 \text{ Log } [Na+] + 0.41(\% G+C) - 0.63(\% \text{ formamide}) - 600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 μg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 μg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 μg/ml denatured salmon sperm DNA at 42° C., and washed in 0.1×SSC and 0.5% SDS at 65° C. for 15 minutes.

The term "oligonucleotide" or "oligo" as used herein means a short sequence of DNA or DNA derivatives typically 8 to 35 nucleotides in length, primers, or probes. An oligonucleotide can be derived synthetically, by cloning or by amplification. An oligo is defined as a nucleic acid molecule comprised of two or more ribo- or deoxyribonucleotides, preferably more than three. The exact size of the oligonucleotide will depend on various factors and on the particular application and use of the oligonucleotide. The term "derivative" is intended to include any of the above described variants when comprising an additional chemical moiety not normally a part of these molecules. These chemical moieties can have varying purposes including, improving solubility, absorption, biological half life, decreasing toxicity and eliminating or decreasing undesirable side effects.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

An "siRNA" refers to a molecule involved in the RNA interference process for a sequence-specific post-transcriptional gene silencing or gene knockdown by providing small interfering RNAs (siRNAs) that has homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting production of the mRNA encoding the protein products listed in Table 1 may be between 15-35 nucleotides in length, and more typically about 21 nucleotides in length.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, peptide-tethering, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the T1D specific marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the T1D specific marker gene nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism," or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long. "Sample" or "patient sample" or "biological sample" generally refers to a sample which may be tested for a particular molecule, preferably a T1D specific marker molecule, such as a marker shown in Table 1. Samples may include but are not limited to cells, body fluids, including blood, serum, plasma, urine, saliva, tears, pleural fluid and the like.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, small molecules, antibodies, peptides, peptide/DNA complexes, and any nucleic acid based molecule, for example an oligo, which exhibits the capacity to modulate the activity of the CNV containing nucleic acids described herein or their encoded proteins. Agents are evaluated for potential biological activity by inclusion in screening assays described herein below.

The term "modulate" as used herein refers increasing or decreasing. For example, the term modulate refers to the ability of a compound or test agent to interfere with signaling or activity of a gene or protein of the present invention. Therefore, modulating the signaling mediated by a protein product listed in Table 1 means that an agent or compound inhibits or enhances the activity of the proteins encoded by the gene. This includes altering the activity of natural killer cells, and preventing autoimmune beta cell destruction.

Methods of Using T1D-Associated CNVs for T1D Detection Assays

T1D CNV containing nucleic acids, including but not limited to those listed in Table 1, may be used for a variety of purposes in accordance with the present invention. T1D-associated CNV containing DNA, RNA, or fragments thereof may be used as probes to detect the presence of and/or expression of T1D specific markers. Methods in which T1D specific marker nucleic acids may be utilized as probes for such assays include, but are not limited to: (1) in situ hybridization; (2) Southern hybridization (3) northern hybridization; and (4) assorted amplification reactions such as polymerase chain reactions (PCR).

Further, assays for detecting T1D-associated CNVs may be conducted on any type of biological sample, including but not limited to body fluids (including blood, urine, serum, gastric lavage), any type of cell (such as white blood cells, mononuclear cells) or body tissue.

From the foregoing discussion, it can be seen that T1D associated CNV containing nucleic acids, vectors expressing the same, T1D CNV containing marker proteins and anti-T1D specific marker antibodies of the invention can be used to detect T1D associated CNVs in body tissue, cells, or fluid, and alter T1D CNV containing marker protein expression for purposes of assessing the genetic and protein interactions involved in T1D.

In most embodiments for screening for T1D-associated CNVs, the T1D-associated CNV containing nucleic acid in the sample will initially be amplified, e.g. using PCR, to increase the amount of the template as compared to other sequences present in the sample. This allows the target sequences to be detected with a high degree of sensitivity if they are present in the sample. This initial step may be avoided by using highly sensitive array techniques that are becoming increasingly important in the art.

Alternatively, new detection technologies can overcome this limitation and enable analysis of small samples containing as little as 1 µg of total RNA. Using Resonance Light Scattering (RLS) technology, as opposed to traditional fluorescence techniques, multiple reads can detect low quantities of mRNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

Thus, any of the aforementioned techniques may be used to detect or quantify T1D-associated CNV marker expression and accordingly, detect patient susceptibility for developing T1D.

Kits and Articles of Manufacture

Any of the aforementioned products can be incorporated into a kit which may contain an T1D-associated CNV specific marker polynucleotide or one or more such markers immobilized on a Gene Chip, an oligonucleotide, a polypeptide, a peptide, an antibody, a label, marker, or reporter, a pharmaceutically acceptable carrier, a physiologically acceptable carrier, instructions for use, a container, a vessel for administration, an assay substrate, or any combination thereof.

Methods of Using T1D-Associated CNVs for Development of Therapeutic Agents

Since the CNVs identified herein have been associated with the etiology of T1D, methods for identifying agents that modulate the activity of the genes and their encoded products containing such CNVs should result in the generation of efficacious therapeutic agents for the treatment of a variety of disorders associated with this condition.

Several of the identified genes contain regions which provide suitable targets for the rational design of therapeutic agents which modulate their activity. Small peptide molecules corresponding to these regions may be used to advantage in the design of therapeutic agents which effectively modulate the activity of the encoded proteins.

Molecular modeling should facilitate the identification of specific organic molecules with capacity to bind to the active site of the proteins encoded by the CNV containing nucleic acids based on conformation or key amino acid residues required for function. A combinatorial chemistry approach will be used to identify molecules with greatest activity and then iterations of these molecules will be developed for further cycles of screening. Molecular modeling should facilitate the identification of specific organic molecules with capacity to bind to the active site of these proteins based on conformation or key amino acid residues required for function. A combinatorial chemistry approach will be used to identify molecules with greatest activity and then iterations of these molecules will be developed for further cycles of screening. In certain embodiments, candidate agents can be screening from large libraries of synthetic or natural compounds. Such compound libraries are commercially available from a number of companies including but not limited to Maybridge Chemical Co., (Trevillet, Cornwall, UK), Comgenex (Princeton, N.J.), Microsour (New Milford, Conn.) Aldrich (Milwaukee, Wis.) Akos Consulting and Solutions GmbH (Basel, Switzerland), Ambinter (Paris, France), Asinex (Moscow, Russia) Aurora (Graz, Austria), BioFocus DPI (Switzerland), Bionet (Camelford, UK), Chembridge (San Diego, Calif.), Chem Div (San Diego, Calif.). The skilled person is aware of other sources and can readily purchase the same. Once therapeutically efficacious compounds are identified in the screening assays described herein, they can be formulated in to pharmaceutical compositions and utilized for the treatment of cancer, alone or in combination with agents typically used to treat T1D.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as described above) which have a nonfunctional or altered T1D associated gene. These host cell lines or cells are defective at the polypeptide level. The host cell lines or cells are grown in the presence of drug compound. The rate of cellular metabolism of the host cells is measured to determine if the compound is capable of regulating cellular metabolism in the defective cells. Host cells contemplated for use in the present invention include but are not limited to bacterial cells, fungal cells, insect cells, mammalian cells, and plant cells. The T1D-associated CNV encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

Cells and cell lines suitable for studying the effects of the CNV encoding nucleic acids on glucose metabolism and methods of use thereof for drug discovery are provided. Such cells and cell lines will be transfected with the CNV encoding nucleic acids described herein and the effects on glucagon secretion, insulin secretion and/or beta cell apoptosis can be determined. Such cells and cell lines will also be contacted with the siRNA molecules provided herein to assess the effects thereof on glucagon secretion, insulin secretion and/or beta cell apoptosis. The siRNA molecules will be tested alone and in combination of 2, 3, 4, and 5 siRNAs to identify the most efficacious combination for down regulating the target gene of interest. Cells suitable for these purposes include, without limitation, INS cells (ATCC CRL 11605), PC12 cells (ATCC CRL 1721), MIN6 cells, alpha-TC6 cells and INS-1 832/13 cells (Fernandez et al., J. of Proteome Res. (2007). 7:400-411). Pancreatic islet cells can be isolated and cultured as described in Joseph, J. et al., (J. Biol. Chem. (2004) 279:51049). Diao et al. (J. Biol. Chem. (2005) 280:33487-33496), provide methodology for assessing the effects of the CNV encoding nucleic acids and/or the siRNAs provided herein on glucagon secretion and insulin secretion. Park, J. et al. (J. of Bioch. and Mol. Biol. (2007) 40:1058-68) provide methodology for assessing the effect of these nucleic acid molecules on glucosamine induced beta cell apoptosis in pancreatic islet cells.

A wide variety of expression vectors are available that can be modified to express the novel DNA or RNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in *Saccharomyces* are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/V5&His (Invitrogen); baculovirus vectors such as pVL1392, pVL1393, or pAC360 (Invitrogen); and yeast vectors such as YRP17, YIP5, and YEP24 (New England Biolabs, Beverly, Mass.), as well as pRS403 and pRS413 Stratagene Inc.); Picchia vectors such as pHIL-D1 (Phillips Petroleum Co., Bartlesville, Okla. 74004); retroviral vectors such as PLNCX and pLPCX (Clontech); and adenoviral and adeno-associated viral vectors.

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, Picchia promoters such as the alcohol oxidase promoter, and *Saccharomyces* promoters such as the gal4 inducible promoter and the PGK constitutive promoter.

In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the T1D-associated CNVs of the present invention or functional fragments thereof provide a system in which to screen potential compounds or agents for the ability to modulate the development of T1D. Thus, in one embodiment, the nucleic acid molecules of the invention may be used to create recombinant cell lines for use in assays to identify agents which modulate the functional activity of the genes listed in Table 1. Also provided herein are methods to screen for compounds capable of modulating the function of proteins encoded by the CNV containing nucleic acids described below.

Another approach entails the use of phage display libraries engineered to express fragment of the polypeptides encoded by the CNV containing nucleic acids on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacophore upon which subsequent drug design can be based.

One can bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacophore.

Thus, one may design drugs which have, e.g., improved polypeptide activity or stability or which act as inhibitors, agonists, antagonists, etc. of polypeptide activity. By virtue of the availability of CNV containing nucleic acid sequences described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

In another embodiment, the availability of T1D-associated CNV containing nucleic acids enables the production of strains of laboratory mice carrying the T1D-associated CNVs of the invention. Transgenic mice expressing the T1D-associated CNV of the invention provide a model system in which to examine the role of the protein encoded by the CNV containing nucleic acid in the development and progression towards T1D. Methods of introducing transgenes in laboratory mice are known to those of skill in the art. Three common methods include: (1) integration of retroviral vectors encoding the foreign gene of interest into an early embryo; (2) injection of DNA into the pronucleus of a newly fertilized egg; and (3) the incorporation of genetically manipulated embryonic stem cells into an early embryo. Production of the transgenic mice described above will facilitate the molecular elucidation of the role that a target protein plays in various cellular metabolic processes, including: aberrant lipid deposition, altered cellular metabolism and glucose regulation. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extra-chromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of T1D-associated CNV containing nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated T1D-associated CNV genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extra-chromosomal recombination, which occurs at a frequency approaching 100%, homologous plasmid-chromosome recombination was originally reported to only be detected at frequencies between $10^{-6}$ and $10"^3$. Non-homologous plasmid-chromosome interactions are more frequent occurring at levels $10^5$-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabinofluranosyl)-5-iodou-racil, (FIAU). By this counter selection, the number of homologous recombinants in the surviving transformants can be increased. Utilizing T1D-associated CNV containing nucleic acid as a targeted insertional cassette provides means to detect a successful insertion as visualized, for example, by acquisition of immunoreactivity to an antibody immunologically specific for the polypeptide encoded by T1D-associated CNV nucleic acid and, therefore, facilitates screening/selection of ES cells with the desired genotype.

As used herein, a knock-in animal is one in which the endogenous murine gene, for example, has been replaced with human T1D-associated CNV containing gene of the invention. Such knock-in animals provide an ideal model system for studying the development of T1D.

As used herein, the expression of a T1D-associated CNV containing nucleic acid, fragment thereof, or a T1D-associated CNV fusion protein can be targeted in a "tissue specific manner" or "cell type specific manner" using a vector in which nucleic acid sequences encoding all or a portion of T1D-associated CNV are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific expression of proteins are well known in the art and described herein.

The nucleic acid sequence encoding the T1D-associated CNV of the invention may be operably linked to a variety of different promoter sequences for expression in transgenic animals. Such promoters include, but are not limited to a platelet-derived growth factor B gene promoter, described in U.S. Pat. No. 5,811,633; a brain specific dystrophin promoter, described in U.S. Pat. No. 5,849,999; a Thy-1 promoter; a PGK promoter; a CMV promoter; a neuronal-specific platelet-derived growth factor B gene promoter; and Glial fibrillar acidic protein (GFAP) promoter for the expression of transgenes in glial cells.

Methods of use for the transgenic mice of the invention are also provided herein. Transgenic mice into which a nucleic acid containing the T1D-associated CNV or its encoded protein have been introduced are useful, for example, to develop screening methods to screen therapeutic agents to identify those capable of modulating the development of T1D.

Pharmaceuticals and Peptide Therapies

The elucidation of the role played by the T1D associated CNVs described herein in cellular and glucose metabolism facilitates the development of pharmaceutical compositions useful for treatment and diagnosis of T1D. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

As it is presently understood, RNA interference involves a multi-step process. Double stranded RNAs are cleaved by the endonuclease Dicer to generate nucleotide fragments (siRNA). The siRNA duplex is resolved into 2 single stranded RNAs, one strand being incorporated into a protein-containing complex where it functions as guide RNA to direct cleavage of the target RNA (Schwarz et al, Mol. Cell. 10:537 548 (2002), Zamore et al, Cell 101:25 33 (2000)), thus silencing a specific genetic message (see also Zeng et al, Proc. Natl. Acad. Sci. 100:9779 (2003)).

The invention includes a method of treating T1D in a mammal. An exemplary method entails administering to the mammal a pharmaceutically effective amount of a siRNA specific for a gene target listed in Table 1. The siRNA inhibits the expression of target gene of interest. Preferably, the mammal is a human. The term "patient" as used herein refers to a human.

Specific siRNA preparations directed at inhibiting the expression of a target gene listed in Table 1, as well as delivery methods are provided as a novel therapy to treat T1D. SiRNA oligonucleotides directed to the target gene of interest specifically hybridize with nucleic acids encoding the target gene product and interfere with target gene expression. The siRNA can be delivered to a patient in vivo either systemically or locally with carriers, as discussed below. The compositions of the invention may be used alone or in combination with other agents or genes encoding proteins to augment the efficacy of the compositions.

A "membrane permeant peptide sequence" refers to a peptide sequence which is able to facilitate penetration and entry of the target gene specific inhibitor across the cell membrane. Exemplary peptides include with out limitation, the signal sequence from Karposi fibroblast growth factor exemplified herein, the HIV tat peptide (Vives et al., J Biol. Chem., 272:16010-16017, 1997), Nontoxic membrane translocation peptide from protamine (Park et al., FASEB J. 19(11):1555-7, 2005), CHARIOT® delivery reagent (Active Motif; U.S. Pat. No. 6,841,535) and the antimicrobial peptide Buforin 2.

In one embodiment of the invention siRNAs are delivered for therapeutic benefit. There are several ways to administer the siRNA of the invention to in vivo to treat T1D including, but not limited to, naked siRNA delivery, siRNA conjugation and delivery, liposome carrier-mediated delivery, polymer carrier delivery, nanoparticle compositions, plasmid-based methods, and the use of viruses.

siRNA composition of the invention can comprise a delivery vehicle, including liposomes, for administration to a subject, carriers and diluents and their salts, and/or can be present in pharmaceutically acceptable formulations. This can be necessary to allow the siRNA to cross the cell membrane and escape degradation. Methods for the delivery of nucleic acid molecules are described in Akhtar et al., 1992, Trends Cell Bio., 2, 139; Delivery Strategies for Antisense Oligonucleotide Therapeutics, ed. Akhtar, 1995, Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192; Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule.

The frequency of administration of the siRNA to a patient will also vary depending on several factors including, but not limited to, the type and severity of the T1D to be treated, the route of administration, the age and overall health of the individual, the nature of the siRNA, and the like. It is contemplated that the frequency of administration of the siRNA to the patient may vary from about once every few months to about once a month, to about once a week, to about once per day, to about several times daily.

Pharmaceutical compositions that are useful in the methods of the invention may be administered systemically in parenteral, oral solid and liquid formulations, ophthalmic, suppository, aerosol, topical or other similar formulations. In addition to the appropriate siRNA, these pharmaceutical compositions may contain pharmaceutically-acceptable carriers and other ingredients known to enhance and facilitate drug administration. Thus such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to administer the appropriate siRNA to a patient according to the methods of the invention. The use of nanoparticles to deliver siRNAs, as well as cell membrane permeable peptide carriers that can be used are described in Crombez et al., Biochemical Society Transactions v35:p44 (2007).

Methods of the invention directed to treating T1D involve the administration of a target gene specific siRNA in a pharmaceutical composition. Such siRNA is administered to an individual as a pharmaceutical composition comprising the siRNA and a pharmaceutically acceptable carrier. Pharmaceutically acceptable carriers are well known in the art and include aqueous solutions such as physiologically buffered saline, other solvents or vehicles such as glycols, glycerol, oils such as olive oil or injectable organic esters.

A pharmaceutically acceptable carrier can contain physiologically acceptable compounds that act, for example, to stabilize the siRNA or increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the siRNA.

One skilled in the art appreciates that a pharmaceutical composition comprising siRNA can be administered to a subject by various routes including, for example, orally or parenterally, such as intravenously (i.v.), intramuscularly, subcutaneously, intraorbitally, intranasally, intracapsularly, intraperitoneally (i.p.), intracisternally, intra-tracheally (i.t.), or intra-articularly or by passive or facilitated absorption. The same routes of administration can be used other pharmaceutically useful compounds, for example, small molecules, nucleic acid molecules, peptides, antibodies and polypeptides as discussed hereinabove.

A pharmaceutical composition comprising siRNA inhibitor also can be incorporated, if desired, into liposomes, microspheres, microbubbles, or other polymer matrices (Gregoriadis, Liposome Technology, Vols. I to III, 2nd ed., CRC Press, Boca Raton Fla. (1993)). Liposomes, for example, which consist of phospholipids or other lipids, are nontoxic, physiologically acceptable and metabolizable carriers that are relatively simple to make and administer.

The pharmaceutical preparation comprises a siRNA targeting a gene listed in Table 1 or an expression vector encoding for said siRNA. Such pharmaceutical preparations can be administered to a patient for treating T1D.

Expression vectors for the expression of siRNA molecules preferably employ a strong promoter which may be constitutive or regulated. Such promoters are well known in the art and include, but are not limited to, RNA polymerase II promoters, the T7 RNA polymerase promoter, and the RNA polymerase III promoters U6 and H1 (see, e.g., Myslinski et al. (2001) Nucl. Acids Res., 29:2502 09).

A formulated siRNA composition can be a composition comprising one or more siRNA molecules or a vector encoding one or more siRNA molecules independently or in combination with a cationic lipid, a neutral lipid, and/or a polyethyleneglycol-diacylglycerol (PEG-DAG) or PEG-cholesterol (PEG-Chol) conjugate. Non-limiting examples of expression vectors are described in Paul et al., 2002, Nature Biotechnology, 19, 505; Miyagishi and Taira, 2002, Nature Biotechnology, 19, 497; Lee et al., 2002, Nature Biotechnology, 19, 500-505.

A lipid nanoparticle composition is a composition comprising one or more biologically active molecules independently or in combination with a cationic lipid, a neutral lipid, and/or a polyethyleneglycol-diacylglycerol (i.e., polyethyleneglycol diacylglycerol (PEG-DAG), PEG-cholesterol, or PEG-DMB) conjugate. In one embodiment, the biologically active molecule is encapsulated in the lipid nanoparticle as a result of the process of providing and aqueous solution comprising a biologically active molecule of the invention (i.e., siRNA), providing an organic solution comprising lipid nanoparticle, mixing the two solutions, incubating the solutions, dilution, ultrafiltration, resulting in concentrations suitable to produce nanoparticle compositions.

Nucleic acid molecules can be administered to cells by incorporation into other vehicles, such as biodegradable polymers, hydrogels, cyclodextrins. (see for example Gonzalez et al., 1999, Bioconjugate Chem., 10, 1068-1074; Wang et al., International PCT publication Nos. WO 03/47518 and WO 03/46185), poly(lactic-co-glycolic) acid (PLGA) and PLCA microspheres (see for example U.S. Pat. No. 6,447,796 and US Patent Application Publication No. US 2002130430), biodegradable nanocapsules, and bioadhesive microspheres, or by proteinaceous vectors (O'Hare and Normand, International PCT Publication No. WO 00/53722)

Cationic lipids and polymers are two classes of non-viral siRNA delivery which can form complexes with negatively charged siRNA. The self-assembly PEG-ylated polycation polyethylenimine (PEI) has also been used to condense and protect siRNAs (Schiffelers et al., 2004, Nuc. Acids Res. 32: 141-110). The siRNA complex can be condensed into a nanoparticle to allow efficient uptake of the siRNA through endocytosis. Also, the nucleic acid-condensing property of protamine has been combined with specific antibodies to deliver siRNAs and can be used in the invention (Song et al., 2005, Nat Biotech. 23:709-717).

In order to treat an individual having T1D, to alleviate a sign or symptom of the disease, the siRNA should be administered in an effective dose. The total treatment dose can be administered to a subject as a single dose or can be administered using a fractionated treatment protocol, in which multiple doses are administered over a more prolonged period of time, for example, over the period of a day to allow administration of a daily dosage or over a longer period of time to administer a dose over a desired period of time. One skilled in the art would know that the amount of siRNA required to obtain an effective dose in a subject depends on many factors, including the age, weight and general health of the subject, as well as the route of administration and the number of treatments to be administered. In view of these factors, the skilled artisan would adjust the particular dose so as to obtain an effective dose for treating an individual having T1D.

The effective dose of siRNA will depend on the mode of administration, and the weight of the individual being treated. The dosages described herein are generally those for an average adult but can be adjusted for the treatment of children. The dose will generally range from about 0.001 mg to about 1000 mg.

The concentration of siRNA in a particular formulation will depend on the mode and frequency of administration. A given daily dosage can be administered in a single dose or in multiple doses so long as the siRNA concentration in the formulation results in the desired daily dosage. One skilled in the art can adjust the amount of siRNA in the formulation to allow administration of a single dose or in multiple doses that provide the desired concentration of siRNA over a given period of time.

In an individual suffering from T1D, in particular a more severe form of the disease, administration of siRNA can be particularly useful when administered in combination, for example, with a conventional agent for treating such a disease. The skilled artisan would administer siRNA, alone or in combination and would monitor the effectiveness of such treatment using routine methods such as pulmonary function determination, radiologic, immunologic or, where indicated, histopathologic methods. Other conventional agents for the treatment of diabetes include insulin administration, glucagon administration or agents that alter levels of either of these two molecules. Glucophage®, Avandia®, Actos®, Januvia® and Glucovance® are examples of such agents.

Administration of the pharmaceutical preparation is preferably in an "effective amount" this being sufficient to show benefit to the individual. This amount prevents, alleviates, abates, or otherwise reduces the severity of T1D symptoms in a patient.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

The following examples are provided to illustrate certain embodiments of the invention. They are not intended to limit the invention in any way.

EXAMPLE I

Identification of CNVs Associated with TID in a Pediatric Genome Wide Association Study We recently completed a genome-wide search for copy number variation (CNV) association with the Type 1 Diabetes (T1D) phenotype. The data quality was strictly filtered based on a call rate above 98%, populations of cases and controls which closely stratified based on Ancestry Informative Markers (AIMs) clustering, a standard deviation of normalized intensity below 0.35, low waviness of intensity corresponding with GC content, and a maximum count of 40 CNVs per individual. This resulted in 504 T1D cases, 292 with complete trios and 3979 disease-free controls. Utilizing a Hidden Markov Model (HMM) approach implemented by PennCNV (Wang et al, 2007), the most probable CNV state is reported for a contiguous sequence of SNPs for each individual sample. We first searched for evidence for association of CNVs to any of the previously reported genes that associate with T1D, including but not limited to HLA, INS, PTPN22, CTLA4, KIAA0350 (CLEC16A) PARP1, AGER, and C4A. There was no evidence for CNV association to these specific genes. SNP based whole genome CNV association was subsequently preformed to capture the most significant points in complex CNV overlap between case and control populations. A chi square statistic is applied to the CNV observance of deletion and duplication for each SNP. To present results in a non-redundant manner, statistical local minimums are reported in reference to a region of nominal significance including SNPs residing within 1 MB. We identified regions of deletion and duplication (Table 1) CNVs in T1D using this approach. The most biologically relevant to previously associated T1D pathways are: MAML2, BAK1, CCND1, RERGL, RNASE4, TRPM1, ANBPT1, ETS2, RAB27A, PYGO1, TBC1, DDEF1, SBF2, PTPRT, COL1A1, NGFR, ALPP, KCNS3, KCNK2, TMTC1, MCTP2, PRSS3, SCG, ONECUT1, AK055863, ETV3, EPX, CRLF3, IGFBP4, SORBS1, and BCMO1.

After review, 47 CNV regions that included at least 2 CNV observances validated, of whom 29 resided on genes. To address the potential biological role of these results, functional clustering of independently associated and validated results provided: Immune system (3 loci, 7 CNVs $p=1.9\times10^{-4}$), Insulin (2 loci, 4 CNVs $p=1.6\times10^{-3}$), Pancreas or liver expression (4 loci, 8 CNVs $p=2.3\times10^{-3}$), CNS development (5 loci, 16 CNVs, $p=1.0\times10^{-6}$), Vitamin A (1 loci, 3 CNVs $5.2\times10^{-3}$), Cell cycle signaling (10 loci, 29 CNVs $p=8.0\times10^{-7}$), and Membrane channels (4 loci, 13 CNVs $p=1.6\times10^{-5}$).

Taken together, we have identified 29 genes harboring 80 CNVs in previously associated T1D pathways that involve 70 cases and thus could account for up to 14% of T1D cases. These results suggest that the genetic landscape in the pathogenesis of T1D involves both common and rare CNVs that associate with the T1D phenotypes, where the rare CNVs are highly heterogeneous and unique to the individual families and cluster on genes that are involved with endocrine signaling and development.

TABLE 1

High Confidence associations of loci to 2 or more T1D cases

| Gene Family | CNVR B36 | Gene B36 | Dist | Pvalue | CN | Cs | Cs-Di | Co | Co-Di |
|---|---|---|---|---|---|---|---|---|---|
| Cell Cycle gene | chr11: 95619379-95620715 | MAML2 | 0 | 0.0026 | Del | 9 | 495 | 19 | 3961 |
| Cell Cycle gene | chr6: 33604692-33633658 | BAK | 14643 | 0.0052 | Del | 3 | 501 | 1 | 3978 |
| Cell Cycle gene | chr11: 69172091-69178211 | CCND1 | 0 | 0.035 | Del | 2 | 502 | 1 | 3977 |
| Cell Cycle gene | chr12: 18117011-18207216 | RERGL | 0 | 0.0126 | Del | 2 | 502 | 0 | 3978 |
| Cell Cycle gene | chr14: 20179566-20252640 | ANG | 0 | 0.3125 | Del | 2 | 502 | 8 | 3970 |
| Cell Cycle gene | chr15: 29143717-29172089 | TRPM1 | 0 | 0.0126 | Del | 2 | 502 | 0 | 3978 |
| Cell Cycle gene | chr8: 107736969-108423211 | ANGPT1 | 0 | 0.3125 | Del | 2 | 502 | 8 | 3968 |
| Cell Cycle gene | chr21: 39037914-39074242 | ETS2 | 25477 | 0.0126 | Dup | 2 | 502 | 0 | 3978 |
| Cell Cycle gene | chr15: 53348055-53717834 | RAB27A | 0 | 0.0119 | Dup | 3 | 501 | 2 | 3977 |
| Cell Cycle gene | chr22: 45875872-45882946 | TBC1D22A | 0 | 0.0649 | Dup | 2 | 502 | 2 | 3977 |

TABLE 1-continued

High Confidence associations of loci to 2 or more T1D cases

| Gene Family | CNVR B36 | Gene B36 | Dist | Pvalue | CN | Cs | Cs-Di | Co | Co-Di |
|---|---|---|---|---|---|---|---|---|---|
| CNS Development | chr8: 131388051-131428826 | DDEF1 | 0 | 0.0052 | Del | 3 | 501 | 1 | 3978 |
| CNS Development | chr11: 9907833-9929638 | SBF2 | 0 | 0.0052 | Del | 3 | 501 | 1 | 3978 |
| CNS Development | chr20: 40615725-40718196 | PTPRT | 0 | 0.3122 | Del | 2 | 502 | 8 | 3971 |
| CNS Development | chr17: 44875052-45629290 | COL1A1 | 0 | 0.0126 | Del | 2 | 502 | 0 | 3974 |
| CNS Development | chr2: 232936077-233023552 | ALPP | 0 | 0.0006 | Dup | 6 | 498 | 5 | 3967 |
| Membrane channel | chr2: 18048653-18056323 | KCNS3 | 70947 | 0.0001 | Del | 6 | 498 | 3 | 3972 |
| Membrane channel | chr1: 213463166-213468645 | KCNK2 | 0 | 0.0119 | Del | 3 | 501 | 2 | 3975 |
| Membrane channel | chr12: 29906457-29906761 | TMTC1 | 77498 | 0.2687 | Del | 2 | 502 | 7 | 3968 |
| Membrane channel | chr15: 91967763-92629470 | MCTP2 | 0 | 0.0351 | Del | 2 | 502 | 1 | 3976 |
| Pancreas/Liver | chr9: 33774908-33835079 | PRSS3 | 0 | 0.035 | Dup | 2 | 502 | 1 | 3978 |
| Pancreas/Liver | chr11: 61744703-61760148 | SCGB1D2 | 6152 | 0.0126 | Dup | 2 | 502 | 0 | 3978 |
| Pancreas/Liver | chr15: 50785554-50804739 | ONECUT1 | 23661 | 0.1003 | Dup | 2 | 502 | 3 | 3973 |
| Pancreas/Liver | chr8: 9217544-9304527 | AK055863 | 0 | 0.1397 | Dup | 2 | 502 | 4 | 3969 |
| Immune System | chr1: 155423036-155427970 | ETV3 | 48235 | 0.0126 | Del | 2 | 502 | 0 | 3978 |
| Immune System | chr17: 53625120-53626496 | EPX | 0 | 0.0126 | Del | 2 | 502 | 0 | 3974 |
| Immune System | chr17: 26040486-26188149 | CRLF3 | 0 | 0.0119 | Dup | 3 | 501 | 2 | 3977 |
| Insulin | chr17: 35862733-35871630 | IGFBP4 | 0 | 0.0126 | Del | 2 | 502 | 0 | 3975 |
| Insulin | chr10: 97127095-97391986 | SORBS1 | 0 | 0.0126 | Dup | 2 | 502 | 0 | 3977 |
| Vitamin A | chr16:79822098-79838201 | BCDO | 0 | 0.0052 | Del | 3 | 500 | 1 | 3976 |

Dist: Distance B-36;
Cs: Cases;
Cs-Di: Cases Diploid;
Co: Control;
Co-Di: Control Diploid

EXAMPLE II

The information herein above can be applied clinically to patients for diagnosing an increased susceptibility for developing T1D, and therapeutic intervention. A preferred embodiment of the invention comprises clinical application of the information described herein to a patient. Diagnostic compositions, including microarrays, and methods can be designed to identify the genetic alterations described herein in nucleic acids from a patient to assess susceptibility for developing T1 D. This can occur after a patient arrives in the clinic; the patient has blood drawn, and using the diagnostic methods described herein, a clinician can detect a CNV in at least one of the gene products listed in Table 1 above. The typical age range for a patient to be screened is between 9 and 12 years of age. The information obtained from the patient sample, which can optionally be amplified prior to assessment, will be used to diagnose a patient with an increased susceptibility for developing T1D. Kits for performing the diagnostic method of the invention are also provided herein. Such kits comprise a microarray comprising at least one of the CNVs provided herein in and the necessary reagents for assessing the patient samples as described above.

The identity of T1D-involved genes and the patient results will indicate which variants are present, and will identify those that possess an altered risk for developing T1D. The information provided herein allows for therapeutic intervention at earlier times in disease progression that previously possible. Also as described herein above, the genes listed in Table 1 provide novel targets for the development of new therapeutic agents efficacious for the treatment of T1D. For example, the therapeutic siRNAs described herein can be used to block expression of the gene product based on the patient signal, thereby inhibiting the pancreatic β-cell destruction that occurs in T1D.

REFERENCES

1. Cucca F, Lampis R, Congia M, et al. A correlation between the relative predisposition of MHC class II alleles to type 1 diabetes and the structure of their proteins. Human molecular genetics 2001; 10(19):2025-37.
2. Julier C, Hyer R N, Davies J, et al. Insulin-IGF2 region on chromosome 11p encodes a gene implicated in HLA-DR4-dependent diabetes susceptibility. Nature 1991; 354(6349):155-9.
3. Barratt B J, Payne F, Lowe C E, et al. Remapping the insulin gene/IDDM2 locus in type 1 diabetes. Diabetes 2004; 53(7):1884-9.
4. Bell G I, Horita S, Karam J H. A polymorphic locus near the human insulin gene is associated with insulin-dependent diabetes mellitus. Diabetes 1984; 33(2):176-83.

5. Bottini N, Musumeci L, Alonso A, et al. A functional variant of lymphoid tyrosine phosphatase is associated with type I diabetes. Nature genetics 2004; 36(4):337-8.
6. Smyth D, Cooper J D, Collins J E, et al. Replication of an association between the lymphoid tyrosine phosphatase locus (LYP/PTPN22) with type 1 diabetes, and evidence for its role as a general autoimmunity locus. Diabetes 2004; 53(11):3020-3.
7. Nistico L, Buzzetti R, Pritchard L E, et al. The CTLA-4 gene region of chromosome 2q33 is linked to, and associated with, type 1 diabetes. Belgian Diabetes Registry. Human molecular genetics 1996; 5(7):1075-80.
8. Ueda H, Howson J M, Esposito L, et al. Association of the T-cell regulatory gene CTLA4 with susceptibility to autoimmune disease. Nature 2003; 423(6939):506-11.
9. Vella A, Cooper J D, Lowe C E, et al. Localization of a type 1 diabetes locus in the IL2RA/CD25 region by use of tag single-nucleotide polymorphisms. American journal of human genetics 2005; 76(5):773-9.
10. Leiter E H, Lee C H. Mouse models and the genetics of diabetes: is there evidence for genetic overlap between type 1 and type 2 diabetes? Diabetes 2005; 54 Suppl 2:S151-8.
11. Gunderson K L, Steemers F J, Lee G, Mendoza L G, Chee M S. A genome-wide scalable CNV genotyping assay using microarray technology. Nature genetics 2005; 37(5):549-54.
12. Fisher R A. Statistical Methods for Research Workers. 1958; Hafner, New York, ed. 13.
13. de Bakker P I, McVean G, Sabeti P C, et al. A high-resolution HLA and CNV haplotype map for disease association studies in the extended human MHC. Nature genetics 2006; 38(10):1166-72.
14. Hirschhorn J N, Lohmueller K, Byrne E, Hirschhorn K. A comprehensive review of genetic association studies. Genet Med 2002; 4(2):45-61.
15. Finn R D, Mistry J, Schuster-Bockler B, et al. Pfam: clans, web tools and services. Nucleic acids research 2006; 34(Database issue):D247-51.
16. Cambi A, Figdor C G. Levels of complexity in pathogen recognition by C-type lectins. Current opinion in immunology 2005; 17(4):345-51.

While certain of the preferred embodiments of the present invention have been described and specifically exemplified above, it is not intended that the invention be limited to such embodiments. It will be apparent to one skilled in the art that various changes and modifications can be made therein without departing from the scope of the present invention, as set forth in the following claims.

The invention claimed is:

1. A method for detecting the presence of at least one nucleic acid harboring a type I diabetes (T1D) copy number variation (CNV), said method consisting of:
   a) obtaining a nucleic acid sample isolated from a patient; and
   b) detecting whether T1D CNVs consisting of a deletion on chromosome 11 in a MAML2 gene between positions 95619379-95620715;
   a deletion on chromosome 6 in a BAK gene between positions 33604692-33633658;
   a deletion on chromosome 11 in a CCND1 gene between positions 69172091-69178211;
   a deletion on chromosome 12 in a RERGL gene between positions 18117011-18207216;
   a deletion on chromosome 15 in a TRPM1 gene between positions 29143717-29172089;
   a deletion on chromosome 8 in a DDEF1 gene between positions 131388051-131428826;
   a deletion on chromosome 11 in a SBF2 gene between positions 9907833-9929638;
   a deletion on chromosome 17 in a COL1A11 gene between positions 44875052-45629290;
   a deletion on chromosome 2 in a KCNS3 gene between positions 18048653-18056323;
   a deletion on chromosome 1 in a KCK2 gene between positions 213463166-213468645;
   a deletion on chromosome 15 in a MCTP2 gene between positions 91967763-92629470;
   a deletion on chromosome 1 in a ETV3 gene between positions 155423036-155427970;
   a deletion on chromosome 17 in an EPX gene between positions 53625120-53626496;
   a deletion on chromosome 17 in a IGFBP4 gene between positions 35862733-35871630;
   a deletion on chromosome 16 in a BCDO gene between positions 79822098-79838201;
   a duplication on chromosome 21 in a ETS2 gene between positions 39037914-39074242;
   a duplication on chromosome 15 in a RAB27 gene between positions 53348055-53717834;
   a duplication on chromosome 2 in a ALPP gene between positions 232936077-233023552;
   a duplication on chromosome 9 in a PRSS3 gene between positions 33774908-33835079;
   a duplication on chromosome 11 in a SCGB1D2 gene between positions 61744703-61760148;
   a duplication on chromosome 17 in a CRLF3 gene between positions 26040486-26188149; and
   a duplication on chromosome 10 in a SORBS1 gene between positions 97127095-97391986; are present, the said T1D CNV's being detected via a method selected from the group consisting of
   i) detectable labeling and size analysis,
   ii) hybridization of allele specific probes,
   iii) allele-specific primer extension,
   iv) oligomer ligation,
   v) DNA sequencing,
   vi) single-stranded conformation polymorphism detection, and
   vii) quantitative PCR using primers specific for the nucleic acids comprising said CNVs.

* * * * *